United States Patent [19]

Ranford

[11] Patent Number: 5,106,372
[45] Date of Patent: Apr. 21, 1992

[54] SINGLE USE SYRINGE

[75] Inventor: Alan B. Ranford, St. Louis, Mo.

[73] Assignee: Sherwood Medical Company, St. Louis, Mo.

[21] Appl. No.: 695,152

[22] Filed: May 3, 1991

[51] Int. Cl.⁵ .............................................. A61M 5/00
[52] U.S. Cl. .................................. 604/110; 604/218; 604/220
[58] Field of Search ............... 604/110, 187, 218, 228, 604/220

[56] References Cited

U.S. PATENT DOCUMENTS

| | | |
|---|---|---|
| 3,114,135 | 12/1963 | Sarnoff . |
| 4,367,738 | 1/1983 | Legendre et al. . |
| 4,391,272 | 7/1983 | Staempfli .................... 604/110 |
| 4,493,703 | 1/1985 | Butterfield .................... 604/110 |
| 4,713,056 | 12/1987 | Butterfield .................... 604/110 |
| 4,731,068 | 3/1988 | Hesse .......................... 604/110 |
| 4,775,363 | 10/1988 | Sandsdalen .................. 604/110 |
| 4,775,364 | 10/1988 | Alles .......................... 604/110 |
| 4,781,684 | 11/1988 | Trenner ..................... 604/218 X |
| 4,790,822 | 12/1988 | Haining ....................... 604/110 |
| 4,808,169 | 2/1989 | Haber et al. ................. 604/195 |
| 4,820,272 | 4/1989 | Palmer ........................ 604/110 |
| 4,826,484 | 5/1989 | Haber et al. ................. 604/110 |
| 4,915,692 | 4/1990 | Verlier ........................ 604/110 |
| 4,923,443 | 5/1990 | Greenwood et al. ............ 604/110 |
| 4,932,941 | 6/1990 | Min et al. .................... 604/110 |
| 4,950,243 | 8/1990 | Estruch .................... 604/218 X |
| 4,961,728 | 10/1990 | Kosinski ...................... 604/110 |

FOREIGN PATENT DOCUMENTS

WO88/10127 12/1988 PCT Int'l Appl. .
WO89/02287 3/1989 PCT Int'l Appl. .

*Primary Examiner*—John D. Yasko
*Attorney, Agent, or Firm*—Andrew J. Beck; Montgomery W. Smith; Richard D. Allison

[57] ABSTRACT

A single use syringe assembly is provided and includes an elongate and generally cylindrical syringe barrel having a preferably annularly shaped ring member near the substantially closed distal end thereof. A plunger assembly is provided and includes an elongate plunger rod having a plunger tip and a locking disc on the distal end thereof and a compressible piston member mounted on the plunger tip of the plunger rod. The piston member includes a proximal recess therein to receive the plunger tip of the plunger rod therein. When the plunger assembly is moved distally and proximally in the syringe barrel during normal use, the piston member may be moved between the distal and proximal ends of the syringe barrel without disabling the syringe assembly. When the user desires to disable the syringe assembly, the plunger assembly is initially moved distally in the syringe barrel until the piston member contacts the distal end of the syringe barrel to expel the contents of the syringe assembly. Next, the distal movement of the plunger rod may be continued so that the plunger tip moves to a second position within the proximal recess of the piston member to move the locking disc on the plunger rod distally of the ring member on the syringe barrel. In this position, the proximal movement of the plunger assembly is prevented and the syringe assembly is disabled.

22 Claims, 3 Drawing Sheets

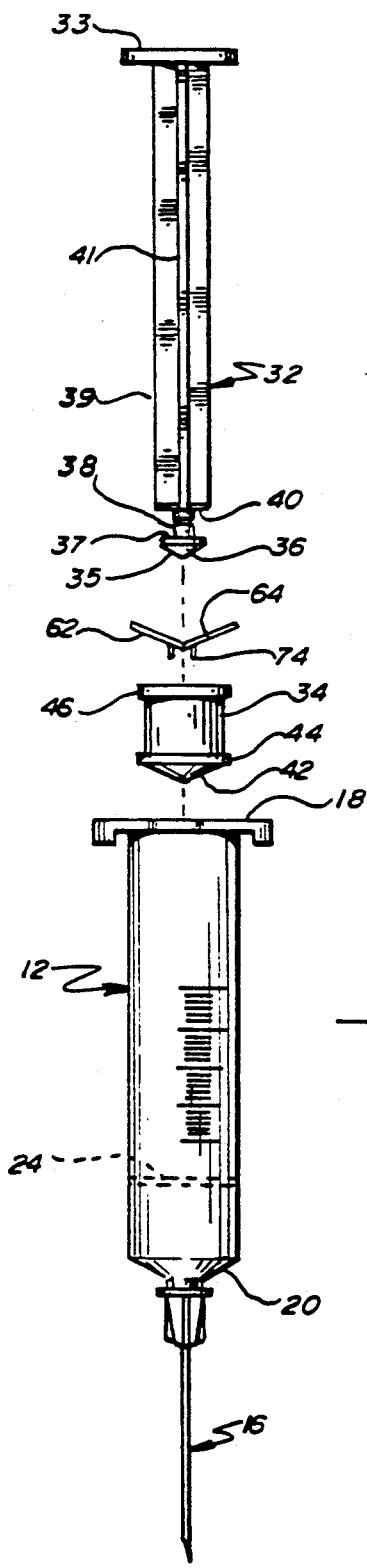
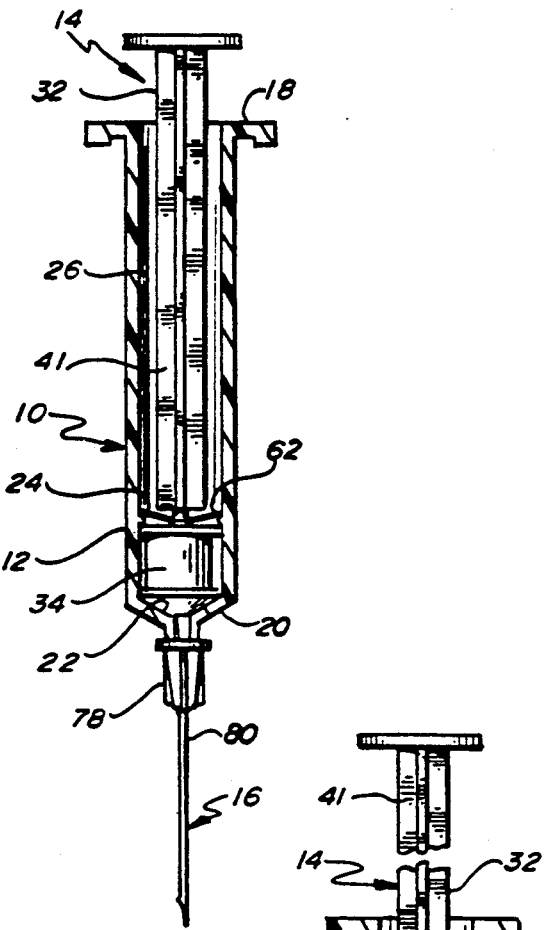
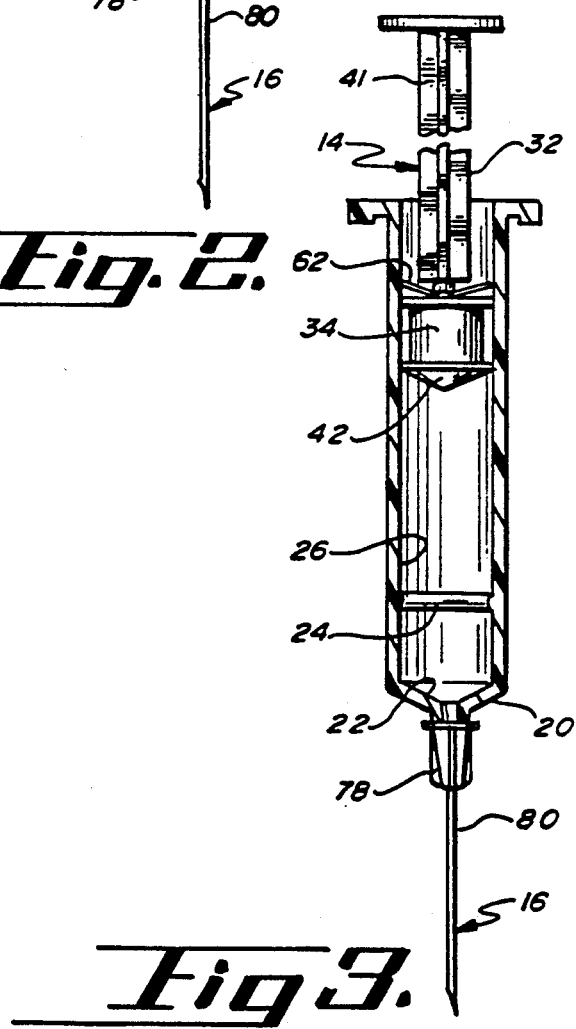
Fig.1.
Fig.2.
Fig.3.

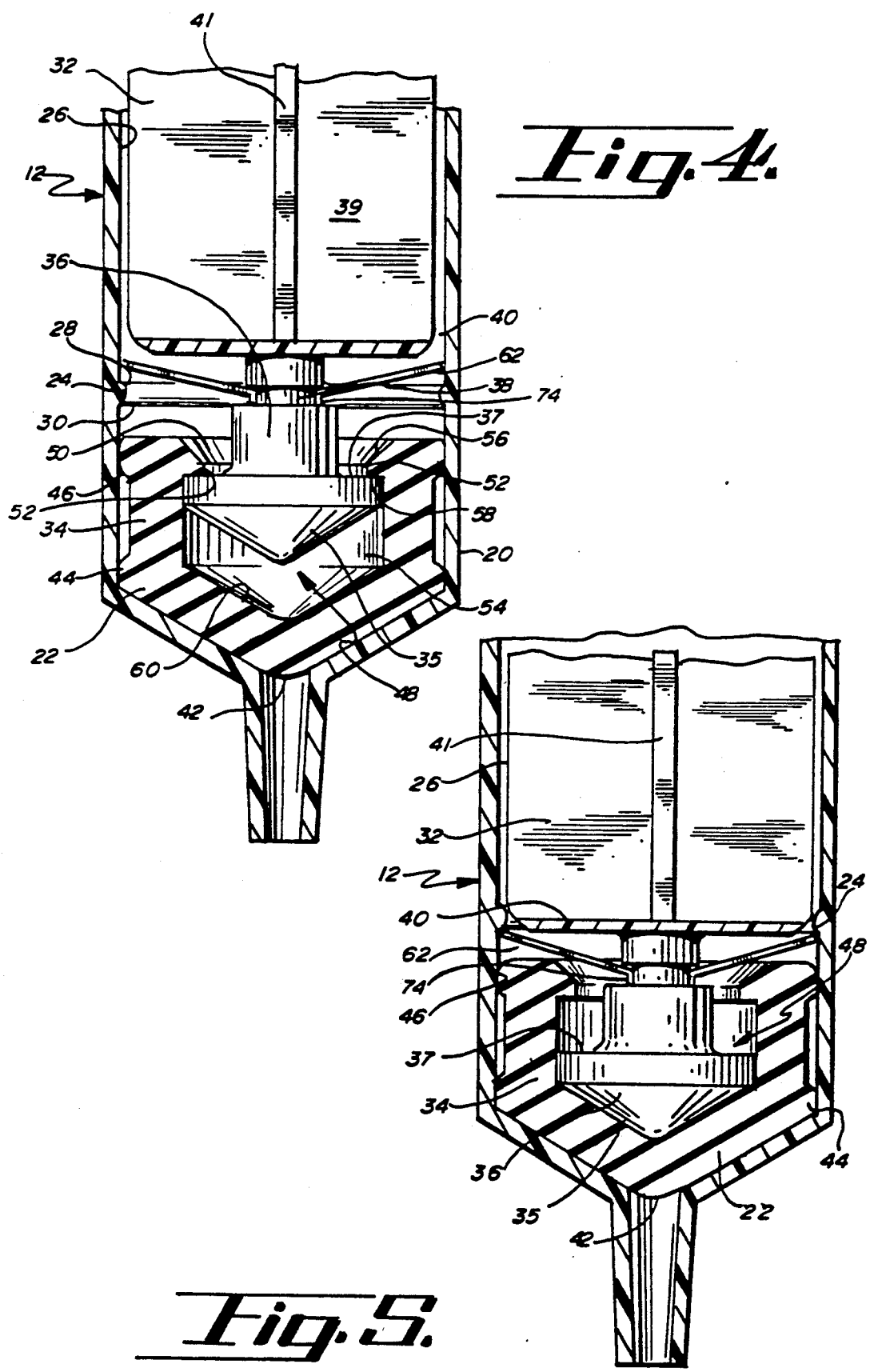

SINGLE USE SYRINGE

FIELD OF THE INVENTION

The present invention relates to a syringe and more particularly to a disposable single-use syringe wherein the plunger and plunger rod may be locked in the distal end of the syringe barrel after use.

BACKGROUND OF THE INVENTION

The majority of syringes used today for medical or laboratory purposes are disposable and are intended to be discarded after a single use. With the increased awareness concerning the potential for the transmission of the AIDS virus and other infectious diseases, a number of different devices have been proposed to disable the syringe after a single use so that drug abusers or other people may not use the same disposable syringe for multiple injections.

The prior art teaches various methods and apparatuses for disabling the syringe and/or needle so that the syringe may not be reused. A number of these constructions teach the destruction of the inner surface of the syringe barrel as the medication is dispensed from the syringe. A syringe of this type is disclosed in U.S. Pat. No. 4,961,728 granted to Kosinski, wherein a longitudinal locking member having a plurality of radially outwardly directed barb members is mounted on the plunger rod of the syringe. As disclosed in this patent, the barb members allow for a one time withdrawal of the plunger rod proximally in the syringe barrel to a limited maximum volume. As the medication is dispensed from the syringe, the locking member is seated in position along the plunger rod and if the subsequent withdrawal of the plunger rod is attempted, the inner surface of the locking member will engage portions of the plunger rod, while the barb member engage the inner surface of the syringe barrel.

Another approach to solving this problem is disclosed in U.S. Pat. No. 4,961,728 granted to Trenner. The device disclosed in Trenner provides an annular groove near the distal end of the syringe barrel having diameter which is greater than the diameter of the cylindrical inner surface of the barrel. A circular locking element is positioned between the stopper and the plunger rod. The outer diameter of the locking element is larger than the inside diameter of the barrel so that when the plunger rod is moved to the distal end of the barrel, the locking element engages the annular groove and prevents withdrawal of the piston tip from the distal end of the barrel. As disclosed in this patent, if the plunger rod is withdrawn from the syringe barrel when the locking element is seated in the annular groove, the locking element will cause the piston tip to separate from the plunger rod. The use of an annular groove on the inner surface of the syringe barrel effectively eliminates the possibility of having a syringe barrel with a ramp-type of plunger stop near the proximal end of the syringe barrel because the core pin necessary to create the groove cannot be removed from the syringe barrel over a ramp-type member near the proximal end of the syringe barrel.

Although the above-described references provide a single-use syringe which is adequate for most uses, a need remains for a single use syringe which is inexpensive and which may be easily manufactured and assembled.

SUMMARY OF THE INVENTION

An advantage of the present invention is that it allows for the assembly of a single-use syringe without significantly departing from the current methods of assembling or manufacturing a conventional syringe.

A further advantage of the present invention is that the syringe of the present invention need not be destroyed if the user accidentally withdraws the plunger rod in the syringe barrel prior to use.

Yet another advantage of the present invention is that the syringe is not disabled unless the user positively pushes the plunger rod to the distal end of the syringe barrel after the piston member has been positioned at the distal end of the syringe barrel.

The present invention provides a simple single-use syringe having an elongate and cylindrical syringe barrel with a plunger assembly which includes a plunger rod, a piston member and a locking disc. The syringe barrel preferably includes one or more annular ramp-shaped surfaces on the inner surface thereof spaced apart from the distal and proximal ends of the syringe barrel. The plunger rod is a conventional elongate member having a plunger tip and neck area on the distal end thereof and a plurality of radially extending rib members extending longitudinally therealong. The piston member is a compressible member having a pair of radially extending sealing lips and a proximal recess adapted to receive and retain the plunger tip of the plunger rod therein. The locking disc is preferably an elliptically-shaped member having a slot therein to allow the locking disc to be slid laterally onto the plunger rod once the piston member has been assembled thereon. In the preferred form of the locking disc, the sides of the widest portion of the locking disc are folded upwardly and are sized to engage the ramp-shaped surfaces on the inner surface of the syringe barrel.

When the single-use syringe of the present invention has been assembled, the syringe assembly may be operated in a manner nearly identical to a conventional syringe wherein fluid is aspirated into the syringe assembly as the plunger rod is moved proximally in the syringe barrel and fluid is dispensed from the syringe as the plunger rod is moved distally in the syringe barrel. In one form of the present invention, a pair of inwardly directed ramp-shaped ring members are formed on the inner surface of the syringe barrel. One of the ring members is positioned near the open proximal end of the syringe barrel while the other ring member is spaced proximally from the reduced diameter distal end of the syringe barrel. With both ring members, the distal side of the ring members are gradually sloped. Additionally, the proximal surface of the proximal ring member is preferably more steeply sloped than the distal surface of the proximal ring member while the proximal surface of the distal ring member may have generally the same gradual slope as the distal surface of the distal ring member. The distal movement of the distal end of the plunger assembly over either of the ring members will cause the widest portion of the locking disc to gradually flex inwardly. Any attempt to move the piston member and locking disc proximally over either of the ring members will be prevented by contact between the widest portion of the locking disc and the proximal surface of the respective ring member.

In the present invention, the interior of the proximal recess on the piston member is longitudinally larger than the plunger tip on the distal end plunger rod.

Therefore, when the piston member is moved to the distal end of the syringe barrel to expel the fluid from the syringe barrel, the plunger rod may be moved further distally in the syringe barrel to move the locking disc over the distal ramp-shaped member to prevent the reuse of the syringe without requiring the user to longitudinally compress the piston member to actuate the locking mechanism.

The proximal recess in the piston member may also include an inwardly directed annular detent therein to frictionally retain the plunger tip of the plunger rod proximally thereof during normal use of the syringe. The annular detent is sized so that the plunger tip is retained proximally therof during normal use of the syringe. When the piston member is positioned at the distal end of the syringe barrel, the locking disc may be moved distally over the distal ring member by moving the plunger rod distally in the syringe barrel so that the plunger tip is moved distally past the annular detent in the piston member.

BRIEF DESCRIPTION OF THE DRAWINGS

FIG. 1 is an exploded side view of the present invention;

FIG. 2 is an assembled side view showing the present invention partially in cross-section and prior to use;

FIG. 3 is a partial side view, in cross-section, showing the present invention with the plunger assembly proximally positioned in the syringe barrel;

FIG. 4 is a partial side view, in cross-section, of the present invention showing the plunger assembly distally positioned in the syringe barrel prior to disabling the plunger assembly in the syringe barrel;

FIG. 5 is a partial side view, in cross-section, of the present invention showing the plunger assembly disabled in the syringe barrel;

DETAILED DESCRIPTION OF THE INVENTION

Figure 6:
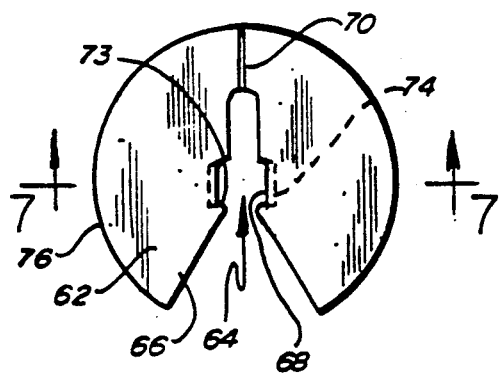
FIG. 6 is an elevated view of the locking disc of the present invention.

As shown in the drawings, the single-use syringe of the present invention is described herein as a syringe assembly 10 comprising a hollow elongated syringe barrel 12 with an elongate plunger assembly 14 reciprocally received therein. The terms "distal" or "distal end" are used herein to define the part or surface of an element which is facing the patient or positioned furthest from the user as described hereinafter. The term "proximal" or "proximal end" are used herein to define the part of surface of an element which is facing away from the patient or positioned closest to the user.

As shown in FIGS. 1-5, the syringe barrel 12 of the preferred embodiment is an elongate tubular member having an open proximal end 18 with a pair of radially extending finger members thereon and a partially closed or reduced diameter distal end 20. The outer surface of the distal end 20 is adapted to receive the needle assembly 16 mounted thereon and includes an opening therein to provide fluid communication between the syringe barrel 12 and the needle assembly 16. The inner surface of the distal end 20 has a tapered and reduced diameter section which forms a shoulder area 22 to receive the distal portion of the plunger assembly 14 adjacent thereto as described hereinafter.

As best shown in FIGS. 2-5, an inwardly directed distal ring member 24 extends inwardly from the inner surface 26 of the syringe barrel 12. The distal ring member 24 is spaced apart a predetermined distance from the distal end 20 of the syringe barrel 12. The distal ring member 24 is preferably comprised of a gradually sloped proximal surface 28 which extends inwardly from the inner surface 26 of the syringe barrel 12 at a preferred angle of about 30° and a similarly sloped distal surface 30 which extends from the inner surface 26 of the syringe barrel at a preferred angle of about 30°. It is anticipated that the angle of the proximal and distal surfaces, 28 and 30 respectively, may be in the range of about 15° to 60° without adversely affecting the operation of the present invention.

The plunger assembly 14 of the preferred embodiment includes an elongate plunger rod 32 and a elastomeric piston member 34. The proximal portion of the plunger rod 32 includes an enlarged head portion 33 which is adapted to be grasped by the user. The distal portion of the plunger rod 32 includes a tapered and cylindrically-shaped plunger tip 36 having a generally conically-shaped distal surface 35 and a perpendicularly oriented proximal surface 37 thereon. A reduced diameter neck portion 38 extends between the plunger tip 36 and the body portion 39 of the plunger rod 32. The body portion 39 of the plunger rod 32 includes a plurality of radially extending longitudinal rib members 41 integral therewith and a circular end member 40 on the distal end of the body portion 39.

The piston member 34 is a generally cylindrically-shaped member which is constructed of a resilient material such as butyl rubber. The distal end 42 of the piston member 34 is tapered and sized to conform to the shoulder area 22 on the distal end 20 of the syringe barrel 12. The outer circumference of the piston member 34 includes distal and proximal annular lip members, 44 and 46 respectively, which sealingly contact the inner surface 26 of the syringe barrel 12. A centrally positioned proximal recess 48 extends into the proximal end of the piston member 34. The proximal recess 48 includes a proximal first section 50 having a radially inwardly directed lip member 52 and a distal second section 54 forming a longitudinally enlarged recessed area in the piston member 34. As shown in the drawings, the proximal side 56 of the lip member 52 is tapered inwardly to facilitate the insertion of the plunger tip 36 into the proximal recess 48. The distal side 58 of the lip member 52 is oriented generally perpendicular to the lip member 52 to retain the proximal surface 37 of the plunger tip 36 distally thereof. The longitudinal and circumferential dimensions of the proximal recess 48 are chosen so that the plunger tip 36 may move longitudinally therein from a first position to a second position as described hereinafter. The distal surface 60 of the proximal recess 48 is shaped to conform to the distal surface 35 of the plunger tip 36 and the distal surface 42 of the piston member 34 is similarly shaped to conform to the shoulder area 22 on the distal end 20 of the syringe barrel 12.

Figure 7:
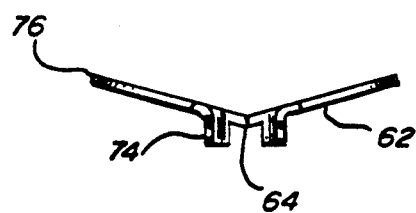
FIG. 7 is a cross-sectional view of the locking disc of the present invention, taken generally along lines 7—7 of FIG. 6.

As shown best in FIGS. 6 and 7, the locking disc 62 of the present invention is preferably a slightly elliptically-shaped member having a generally V-shaped cross-section as shown in FIG. 7. The locking disc 62 is preferably constructed of a material that is harder than the polypropylene syringe barrel 12 or plunger rod 32 and the elastomeric piston member 34. One such preferred material is stainless steel. The locking disc 62 preferably includes an elongate slot 64 therein which consists of a first tapered section 66, a second positioning section 68 and a reduced-width third section 70. The sides of the tapered section 66 taper inwardly from the outer circumference of the locking disc 62 to the positioning section 68 of the slot 64. The width of the positioning section 68 of the slot 64 includes an inner shoulder area 72 adjacent to the third section 70 of the slot 64 and a pair of inwardly directed tab members 73 which form a space therebetween that is slightly narrower than the neck portion 38 of the plunger rod 32. The positioning section 68 is sized so that the center of the positioning section 68 is centrally located on the locking disc 62 and so that the neck portion 38 of the plunger rod is retained between the shoulder area 72 and the tab members 73. Preferably, a flange 74 is added to the positioning section 68 of the locking disc 62 to surround and strengthen the positioning section 68 and shoulder area 72 of the locking disc 62 as described more fully hereinafter. The third section 70 of the slot 64 extends inwardly beyond the center of the locking disc 62 and has a generally uniform width which is smaller than the width of the positioning section 68 of the slot 64. As described more fully below, the primary function of the third section 70 is to minimize the resistance to flexing of the locking disc 62 as the plunger assembly 14 is moved through the syringe barrel 12. As mentioned above, the locking disc 62 preferably has an elliptical shape with the widest portion 76 of the locking disc 62 oriented perpendicularly to the elongate slot 64 and the smallest portion of the locking disc 62 aligned with the elongate slot 64. Alternately, it is anticipated that the locking disc 62 may be shaped in nearly any other manner including with a pair of ears or flanges (not shown) oriented perpendicularly to the slot 64 of the locking disc 62 so that the contact between the proximal surface 28 of the distal ring member 24 is minimized while maintaining sufficient contact between the locking disc 62 and the distal surface 30 of the ring member 24 to retain the plunger assembly 14 in the locked position as described hereinafter.

The needle assembly 16 consists of a conventional needle hub 78 and needle cannula 80. The needle hub 78 is adapted to be removably or permanently mounted on the distal end 20 of the syringe barrel 12. The needle cannula 80 extends distally from the needle hub 78 and includes a skin piercing needle point thereon.

Assembly of the present invention may be accomplished without significantly altering the assembly steps of a conventional syringe. This is particularly important in view of the fact that the manufacture and assembly of conventional syringes is highly automated and modifications to the assembly procedure may be very expensive and time consuming. With the syringe assembly 10 of the present invention, the syringe barrel 12 and the plunger assembly 14 may be formed and assembled in the conventional manner with the exception that the locking disc 62 is laterally inserted onto the plunger assembly 14 between the piston member 34 and the circular end member 40 on the plunger rod 32 prior to the insertion of the plunger assembly 14 into the syringe barrel 12. As shown in the drawings, once the plunger tip 36 has been inserted into the proximal recess 48 on the piston member 34, the slot 64 of the locking disc 62 may be aligned with the neck portion 38 of the plunger rod 32. The neck portion 38 of the plunger rod 32 may then be inserted through the tapered section 66 of the slot 64 and into the positioning section 68 of the slot 64 so that the flange 74 is positioned adjacent to the neck portion 38 of the plunger rod 32 and the neck portion 38 of the plunger rod 32 is positioned inwardly of the tab members 73.

The locking disc 62 is preferably preshaped prior to the placement of locking disc 62 on the plunger assembly 14 so that the contact between the widest portion 76 of the locking disc 62 and the inner surface 26 of the syringe barrel 12 is consistently maintained. In the preferred form of the present invention, the portion of the locking disc 62 adjacent to and opposite the tapered section 66 of the slot 64 does not contact the inner surface 26 of the syringe barrel 12 during movement of the plunger assembly 14 in the syringe barrel 112. Therefore, any resistance to the movement of the plunger assembly 14 in the syringe barrel 12 between the locking disc 62 and the inner surface 26 of the syringe barrel 12 is minimized. Additionally, the preferred diameter of the locking disc 62 along the axis of the elongate slot 62 is preferably less than the diameter of the ring member 24 on the syringe barrel 12 so that this portion of the locking disc 62 can pass by the ring member 24 without engaging it.

In use, the syringe assembly 10 may be used in a conventional manner to receive medication or body fluids therein. As shown in the drawings, during the conventional use of the present embodiment, the proximal surface 37 of the plunger tip 36 is freely positioned adjacent to the distal side 58 of the lip member 52 in the proximal precess 48. The presence of the gradually tapered distal ring member 24 on the inner surface 26 of the syringe barrel 12 is less likely to break the seal between the distal and proximal lip members, 44 and 46 respectively, on the outer surface of the piston member 34 and the inner surface 26 of the syringe barrel 12 than the presence of an annular groove on the syringe barrel as disclosed in the prior art as the plunger assembly 14 is moved distally and proximally in the syringe barrel 12.

As the medication or other fluid is ejected from the syringe assembly 10, the plunger assembly 14 is moved distally in the syringe barrel 12 until the distal end 42 of the piston member 34 contacts the shoulder area 22 at the distal end 20 of the syringe barrel 12 to expel all of the medication or fluid from the syringe barrel 12. The distal movement of the plunger rod 32 causes the locking disc 62 to slide over the proximal and distal surfaces, 28 and 30 respectively, of the distal ring member 24 so that the widest portion 76 of the locking disc 62 is located distally of the distal ring member 24 in the syringe barrel 12. Once the locking disc 62 is moved distally of the distal ring member 24, any attempted proximal movement of the plunger rod 32 will cause the widest portion 76 of the locking disc 62 to contact the sloped distal surface 30 of the distal ring member 24. Further pulling on the plunger rod 32 in the proximal direction will cause the flange on the locking disc 62 to dig into the distal side of the neck portion 38 of the plunger rod 32 to prevent the plunger rod 32 from being pulled out of the syringe barrel 12.

Figure 8:
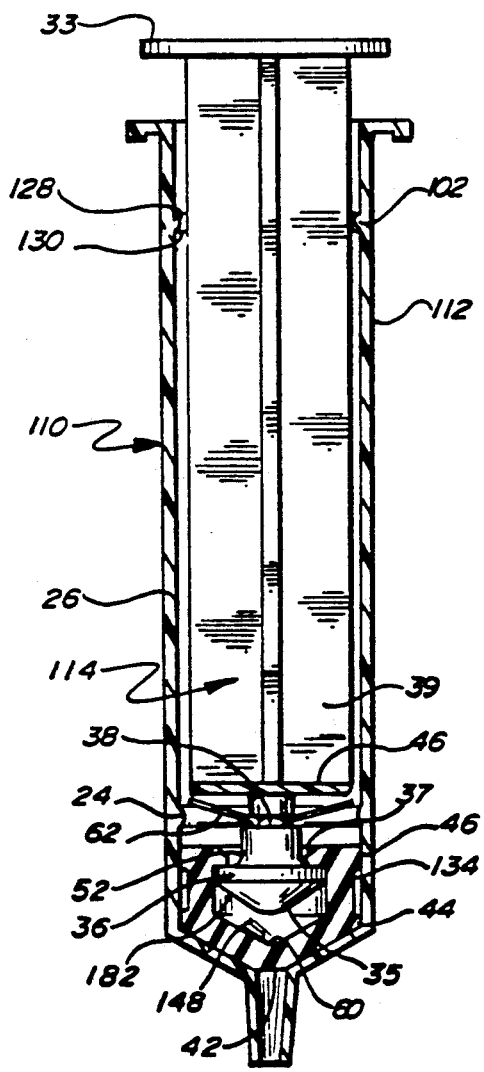
FIG. 8 is a side view, in cross-section, of an alternate embodiment of the present invention showing the plunger assembly distally positioned in the syringe barrel prior to disabling the plunger assembly in the syringe barrel.
Figure 9:
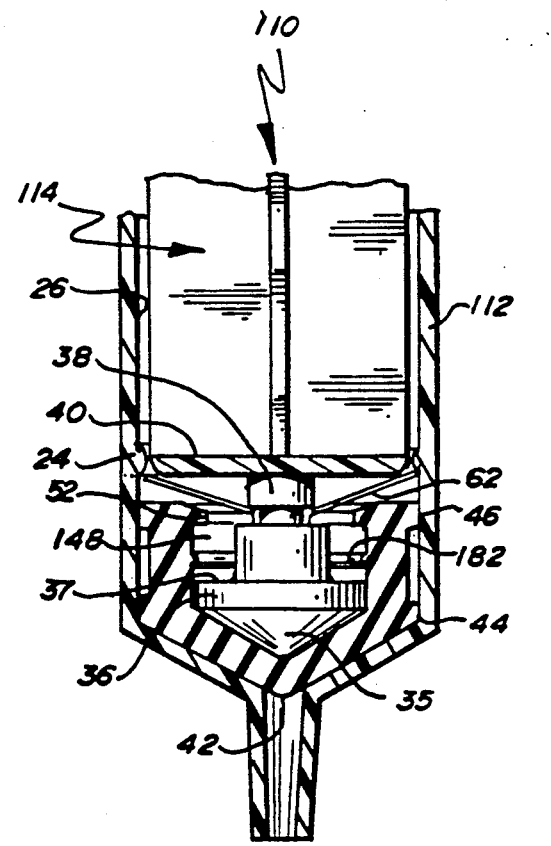
FIG. 9 is a partial side view, in cross-section, of the embodiment shown in FIG. 8 with the plunger assembly disabled in the syringe barrel.

FIGS. 8 and 9 illustrate a further modification or alternate embodiment of the present invention. The syringe assembly 110 of this embodiment operates in a manner similar to the syringe assembly 10 described above with respect to the preferred embodiment and like numbers have been added to like elements. As shown in FIG. 8, the syringe barrel 112 of this embodiment has been modified to include a proximally positioned proximal ring member 102 having a gradually sloped proximal surface 128 and a more steeply sloped distal surface 130. The addition of the proximal ring member 102 to the syringe barrel 112 provides the user with a proximal stop for the plunger assembly 114 to prevent the plunger assembly 114 from being inadvertently or intentionally removed from the syringe barrel 112 once the locking disc 62 has been added to the plunger assembly 114 and inserted into the syringe barrel 112. Therefore, once the plunger assembly 114 is moved proximally in the syringe barrel 112, contact between the locking disc 62 and the proximal ring member 102 will prevent the plunger assembly from being removed from the syringe barrel 112. Additionally, the end member 40 on the distal end of the plunger rod 32 will prevent access to the locking disc 62 once the plunger assembly 114 is inserted into the syringe barrel 112.

Assembly of the present embodiment and the prior embodiment may be accomplished using many of the currently automated steps for the low cost assembly of a syringe. With both embodiments, it is preferable to automatically assemble the plunger assembly by adding the locking disc and piston member to the distal end of the plunge rod prior to the insertion of the plunger rod into the syringe barrel. Alternately, in the present embodiment, the piston member may be inserted into the syringe barrel and then the plunger rod with the locking disc positioned thereon may be inserted into the syringe barrel so that as the plunger rod is inserted into the syringe barrel, the distal end of the plunger rod will engage the piston member. The only difference between this procedure and the current assembly procedure is that the depth of insertion of the plunger rod into the syringe assembly will have to be programmed into the assembly equipment so that the plunger assembly is not automatically inserted to the distal end of syringe barrel to prevent the plunger assembly from being assembled in the locked position as described hereinafter.

Once the syringe assembly 110 of the present embodiment is assembled, the syringe assembly 110 may be packaged, shipped and stored generally in the same manner as a conventional syringe assembly. As shown in FIGS. 8 and 9, the piston member 134 of the present embodiment may include an annular and inwardly directed detent 182 positioned approximately midway along the inner surface of the proximal recess 148. As described more fully hereinafter, the addition of the detent 182 to the proximal recess 148 provide a tactile indication that the piston member 134 is at the distal end of the syringe barrel 112. The detent 182 also eliminates the free motion of the plunger rod 32 relative to the piston member 134 which may occur during use of the prior embodiment.

As shown in FIG. 9, the plunger rod 32 is initially positioned in an initial first position in the piston member 134 wherein the proximal surface 37 of the plunger tip 36 either contacts or is adjacent to the distal side of the lip member 52 in the piston member 134. In this first position, the plunger assembly 114 is freely movable between a proximal position wherein the locking disc 62 contacts the distal surface 130 of the proximal ring member 102 and a distal position wherein the piston member 134 contacts the shoulder area 22 of the syringe barrel 112 (FIG. 8). When the plunger rod 32 and piston member 134 are in the first position. As shown in FIG. 8, the locking disc 62 is positioned proximally of the distal ring member 24. Therefore, the user may repeatedly move the plunger assembly 114 proximally and then distally in the syringe barrel 112 without disabling the syringe assembly 110.

When the user has completed their intended use of the syringe assembly 110, the user may expel all of the fluid from the syringe barrel 112 by returning the plunger assembly 114 to the first position as shown in FIG. 8. Next, the syringe assembly 110 may be disabled by moving the plunger rod 32 to a second position within the piston member 134 wherein the distal surface 35 of the plunger tip 36 either contacts or is adjacent to the distal surface 60 of the proximal recess 148 and the proximal surface 37 of the plunger tip 36 is positioned distally of the detent 182. When the plunger tip 36 is in this second position, the locking disc 62 is positioned distally of the distal ring member 24 and proximal movement of the plunger assembly 114 in the syringe barrel 112 is prevented.

In this embodiment, the locking disc 62 is allowed to travel further in the syringe barrel 112 from the proximal position of the plunger assembly 114 to the distal end of the syringe barrel 112 than the piston member 134 travels in the syringe barrel 112. This is because the piston member 134 does not move in the syringe barrel 112 as the plunger rod 32 is moved from the first position in the proximal recess 148 of the piston member 134 to the second position in the proximal recess 148 of the piston member 134 wherein the plunger assembly 114 is locked in the syringe barrel 112 as described above. Additionally, the distance the plunger tip 36 travels in the proximal recess 148 of the piston member 134 between the first position when the plunger assembly 114 is freely movable in the syringe barrel 112 and the locked second position is preferably equal to or greater than the distance necessary for the locking disc 62 to travel from the unlocked first position of the plunger assembly (FIG. 8) to the locked second position (FIG. 9) wherein the widest portion 76 of the locking disc 62 is positioned distally of the distal surface 30 of the distal ring member 24. This enables the user to move the plunger rod 32 from the first position in the piston member 134 to the locked second position without requiring the user to press the plunger rod 32 into the syringe barrel 112 with sufficient force to compress the piston member 134 in the syringe barrel 112 in order to disable the syringe assembly 110 of the present embodiment.

Although, as described above, the preferred embodiment of the present invention may include a small amount of free motion between the plunger rod 32 and the piston member 34, it is anticipated that the proximal recess 48 of the piston member 34 may also be formed with sufficiently close tolerances such that when the piston member 34 is placed in the syringe barrel 12, the normal radial compression of the piston member 34 in the syringe barrel will create a slight frictional resistance between the piston member 34 and the plunger tip 36 to frictionally retain the plunger tip in the first position within the proximal recess 48 of the piston member 34 in the same manner as described above with respect to the alternate embodiment of the present invention. It is further anticipated that the plunger tip 36 may then be moved to the second position in the proximal recess 48 of the piston member 34 without requiring the user to longitudinally compress the piston member 34 in the syringe barrel 12.

While the presently preferred forms of the present invention have been described in detail herein, it is to be understood that the inventive concepts of the present invention may be variously embodied or employed without departing from the scope of the present invention as defined by the following claims.

What is claimed is:

1. A syringe assembly, comprising:
    a hollow and elongated generally cylindrical barrel means including an inner surface, an open proximal end and a reduced diameter distal end adapted to receive a needle means operatively associated therewith;
    an elongate plunger assembly adapted to be distally and proximally movable in said barrel means wherein said plunger assembly includes an elongate plunger rod having distal and proximal ends thereon and a piston means having a longitudinal axis with distal and proximal ends and said piston means being operatively associated with said distal end of said plunger rod;
    said distal end of said barrel means having a radially inwardly extending wall portion with an opening extending therethrough for communication with said needle means wherein said wall portion provides a stop for the distal movement of said piston means in said barrel means;
    movement preventing means including a first portion movable with said plunger assembly and a second portion operatively associated with said inner surface of said barrel means; and
    said plunger rod adapted to be movable with respect to said piston means from a first position wherein said plunger assembly is movable distally and proximally in said barrel means and said first portion of said movement preventing means is positioned proximally of said second portion of said movement prevention means to a second position wherein said first portion of said movement preventing means is positioned distally of said second portion of said movement preventing means and movement of said plunger assembly is restricted and wherein said distal end of said plunger rod is spaced apart from said distal end of said piston means in said first position.

2. The syringe assembly of claim 1 wherein said plunger rod is distally and longitudinally movable with respect to a portion of said piston means from said first position to said second position.

3. The syringe assembly of claim 1 wherein said distal end of said plunger rod includes a connector means thereon adapted to be received in a recess in said piston means and wherein said connector means is distally movable in said recess from said first position to said second position such that said connector means is adjacent said distal end of said piston means in said second position.

4. The syringe assembly of claim 3 wherein said recess includes a detent means therein to retain said connector means proximally thereof in said first position.

5. The syringe assembly of claim 4 wherein said connector means is retained proximally of said detent means in said second position.

6. The syringe assembly of claim 1 wherein said first portion of said movement preventing means is a locking disc operatively associated with said plunger assembly and said second portion is an inwardly directed first member distally spaced apart from said distal end of said barrel means on said inner surface of said barrel means.

7. The syringe assembly of claim 6 wherein said locking disc is laterally mountable on said plunger assembly between said proximal end of said plunger rod and said piston means.

8. The syringe assembly of claim 6 wherein a second member extends inwardly from a position on said inner surface of said barrel means near said proximal end thereof and said locking disc is movably positioned between said first and second members in said first position.

9. A syringe assembly comprising:
    a hollow and elongated generally cylindrical barrel means including an inner surface, an open proximal end and a reduced diameter distal end adapted to receive a needle means operatively associated therewith;
    an elongate plunger assembly adapted to be distally and proximally movable in said barrel means wherein said plunger assembly includes a longitudinal axis with an elongate plunger rod having distal and proximal ends thereon and a piston means operatively associated with said distal end of said plunger rod and having distal and proximal ends and a receiving means associated therewith;
    said distal end of said barrel means having a radially inwardly extending wall portion with an opening extending therethrough for communication between said barrel means and said needle means wherein said wall portion provides a stop for the distal movement of said piston means in said barrel means;
    connector means on said distal end of said plunger rod wherein said connector means is adapted to be received in said receiving means in said piston means and said connector means is movable from a first position in said receiving means wherein said connector means is spaced apart from said distal end of said piston means to a second position therein;
    movement restricting means including a first portion operatively movable with said plunger assembly and a second portion operatively associated with said inner surface of said barrel means; and
    said first portion of said movement restricting means adapted to be positioned proximally of said second portion of said movement restricting means when said connector means is in said first position and said first portion is adapted to be positioned distally of said second portion when said connector means is in said second position such that said plunger assembly is movable distally and proximally in said barrel means when said connector means is in said first position and movement of said plunger assembly to said proximal end of said barrel means is restricted when said connector is in said second position.

10. The syringe assembly of claim 9 wherein said receiving means is a recess in said proximal end of said piston means and said connector means is positioned adjacent said proximal end of said piston means in said first position and adjacent said distal end of said piston means in said second position.

11. The syringe assembly of claim 9 wherein said receiving means includes an inwardly directed detent means therein and said connector means is positioned proximally thereof in said first position and distally thereof in said second position.

12. The syringe assembly of claim 9 wherein said first portion is more rigid than said second portion of said movement restricting means and said second portion extends radially inwardly from said inner surface of said barrel means.

13. The syringe assembly of claim 12 wherein said second portion is a ring member having distal and proximal surfaces that are tapered inwardly from said inner surface of said barrel means.

14. The syringe assembly of claim 12 wherein said inner surface of said barrel means includes a proximally positioned and radially inwardly directed ring member adapted to retain said first portion of said movement restricting means distally thereof when said connector means is operatively in said first and second positions.

15. The syringe assembly of claim 9 wherein said first portion of said movement restricting means is a locking disc adapted to be laterally mountable on said plunger assembly.

16. The syringe assembly of claim 15 wherein a first circumferential portion of said locking disc is spaced apart from said inner surface of said barrel means.

17. The syringe assembly of claim 15 wherein a second circumferential portion of said locking disc is adapted to engage said second portion of said movement restricting means when said connector means is in said second position.

18. The syringe of claim 15 wherein said locking disc includes contact means thereon to contact said second portion of said movement restricting means when said connector means is in said second position and wherein said second portion comprises a member that extends radially inwardly from said inner surface of said barrel means.

19. The syringe assembly of claim 9 wherein said plunger rod is distally movable in said barrel means when said distal end of said piston means is adjacent said wall portion of said barrel means.

20. A syringe assembly comprising:

a hollow and elongated generally cylindrical barrel means including an inner surface, an open proximal end and a reduced diameter distal end;

an elongate plunger assembly adapted to be distally and proximally movable in said barrel means wherein said plunger assembly includes an elongate plunger rod and a piston means said plunger rod having distal and proximal ends with a connector means extending distally therefrom said connector means having a distal end thereon, said piston means having distal and proximal ends with a recess therein extending distally from said proximal end of said piston means and wherein said recess is adapted to movably receive said connector means therein;

movement restricting means including a disc means operatively positioned on said plunger assembly and a radially inwardly extending first member on said inner surface of said barrel means; and said connector means being movable from a first position in said recess wherein said connector means is adjacent said proximal end of said piston means and said disc means is positioned proximally of said first member such that said plunger assembly is movable distally and proximally in said barrel means to a second position wherein said disc means is positioned distally of said first member and movement of said plunger assembly to said proximal end of said barrel means is restricted.

21. The syringe assembly of claim 20 wherein said recess includes detent means therein wherein a portion of said connector means is positioned proximally of said detent means in said first position and distally of said detent means in said second position.

22. The syringe assembly of claim 20 wherein said first member comprises a first ring member extending radially inwardly from said inner surface of said barrel means and spaced apart from the distal end thereof and wherein a second ring member extends radially inwardly from said inner surface of said barrel means operatively near the proximal end thereof such that said disc means is movably retained therebetween when said connector means is in said first position.

* * * * *